United States Patent [19]

Rosenthale

[11] 4,183,912
[45] Jan. 15, 1980

[54] INHALATION THERAPY FOR RELIEVING BRONCHIAL SPASM USING QUATERNARY SALTS OF PROMETHAZINE

[75] Inventor: Marvin E. Rosenthale, Princeton, N.J.

[73] Assignee: American Home Products Corporation, New York, N.Y.

[21] Appl. No.: 869,408

[22] Filed: Jan. 16, 1978

[51] Int. Cl.² .............................................. A61K 31/54
[52] U.S. Cl. ...................................... 424/45; 424/247
[58] Field of Search ...................... 424/45, 247; 544/41

[56] References Cited

U.S. PATENT DOCUMENTS

| | | | |
|---|---|---|---|
| 2,887,481 | 5/1959 | Sherlock et al. | 260/243 |
| 3,933,822 | 1/1976 | Broughton | 424/45 X |
| 4,016,279 | 4/1977 | Bauer et al. | 424/45 X |
| 4,025,614 | 5/1977 | Snader et al. | 424/45 |

FOREIGN PATENT DOCUMENTS 881379 11/1961 United Kingdom ...................... 544/41

OTHER PUBLICATIONS

Remington's Pharm. Sci., 13th ED., pp. 450 & 1208.

*Primary Examiner*—Leonard Schenkman

[57] ABSTRACT

The use of quaternary salts of promethazine by the inhalation route is described. The thus administered compositions provide new, non-toxic, potent means for relieving bronchial spasm and bronchoconstriction in warm-blooded animals.

5 Claims, No Drawings

INHALATION THERAPY FOR RELIEVING BRONCHIAL SPASM USING QUATERNARY SALTS OF PROMETHAZINE

BACKGROUND OF THE INVENTION

There are at present several commercially available inhalation preparations useful for the treatment of asthma, bronchial spasm, and reversible bronchoconstriction. These preparations are either certain catacholamines in powder form or solution, or a solution of the adrenal cortical steroid, dexamethasone. For administration, the powder is sprayed or the solution is first atomized and then sprayed directly into the nasal or oral opening. In addition, there is an inhalable powder comprising a bis-chromone derivative; however, this medicament has no intrinsic bronchodilator, or anti-histamine activity, and is useful only prophylactically. It is not indicated for treating an acute asthmatic attack. The literature also describes the use of certain prostaglandins by the oral inhalation route for the relief of bronchial spasm. Thus, for example, Belgian Pat. No. 792,216 describes this use for prostaglandin $F_{2\beta}$. The use of certain quaternary salts of atropine as inhalable anticholinergic bronchodilators has been reported; Arzneium.-Forsch. (Drug Res.) 26, 959–1020 (1976). The use of certain quaternized phenothiazines [e.g. 1-(10-phenothiazinylmethyl)ethyl-2-hydroxyethyldimethylammonium chloride, Acta. Pharmacol. et Toxicol., 18, 105 (1961)] as antihistiminics (i.m. administration) has also been studied.

The existing inhalable medicaments useful for the control of asthma, bronchial spasm and similar disorders each, unfortunately, possess deleterious side effects, and a generally useful medicament, indicated for use by all patients requiring inhalation therapy, does not exist.

The catacholamines most often utilized are epinephrine, isoproterenol, and metaproterenol. These adrenergic agents are most powerful and useful drugs in the relief of severe asthmatic spasm (status asthmaticus); however, as with other dilators they have untoward side effects. Some of the more undesirable of these are stimulation of the cardiovascular and central nervous system, hyperglycemia, and tolerance (tachyphylaxis), which greatly reduces the effectiveness of these drugs.

Many cases of asthma and status asthmaticus refractory to usual treatment methods may now be controlled by the use of inhalable dexamethasone. However, long term treatment of asthma with steroids involves the risk of sodium retention, hypertension, ulcers, calcium loss from osseous structures, and other well-known side effects.

Thus, the agents presently available to the physician have a number of problems associated with their use, including toxicity, adverse effect on the cardiovascular system (especially in the sympathomimetics), and fluid retention or edema (with the corticosteroids). Thus, a definite need exists for means employing effective and well-tolerated bronchodilating agents.

The difficulty in finding such agents is well-known to those skilled in the art. It is a matter of common knowledge and experience, for example, that many compounds that relax smooth muscles are not bronchodilators by all common routes of administration (and especially by the aerosol route of administration). For example, for some obscure reason, ephedrine is a smooth muscle relaxant and is an orally active bronchodilator, but not by aerosol; epinephrine, also a smooth muscle relaxant, is used by aerosol but not orally. And aminophylline, a drug which can relax bronchial smooth muscle in vitro or by injection in vivo is inactive as a bronchodilator aerosol. In view of this it is suprising to find new means which, even though characterized by smooth muscle relaxing activity, provide bronchodilation by administration via the aerosol route, possess high levels of activity, and are non-toxic.

The present invention provides new, potent, bronchodilator compositions comprising quaternary salts of the well-known medicament, promethazine, which compositions are useful upon administration by the aerosol route.

SUMMARY OF THE INVENTION

The invention sought to be patented in its principal process aspect resides in the concept of a method of relieving bronchial spasm and facilitating breathing in warm-blooded animals which comprises administering to a warm-blooded animal in need thereof, by aerosol route, an amount sufficient to relieve bronchial spasm and facilitate breathing in said warm-blooded animal of a composition comprising:

(a) a compound of the formula:

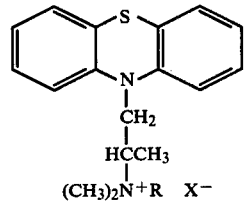

wherein R is hydroxyalkyl of from 2 to 4 carbon atoms with the proviso that the hydroxyl group is not borne on the same carbon atom which is bonded to nitrogen; X is a pharmacologically acceptable anion; and (b) a pharmacologically acceptable carrier.

The invention sought to be patented in its first subgeneric process aspect resides in the concept of a method of relieving bronchial spasm and facilitating breathing in warm-blooded animals which comprises administering to a warm-blooded animal in need thereof, by aerosol route, an amount sufficient to relieve bronchial spasm and facilitate breathing in said warm-blooded animal of a composition comprising:

(a) a compound of the formula:

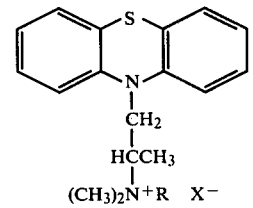

wherein R is hydroxyalkyl of from 2 to 4 carbon atoms with the proviso that the hydroxyl group is not borne on the same carbon atom which is bonded to nitrogen; X is $OH^-$, $Cl^-$, $Br^-$, $I^-$, $NO^-_3$,

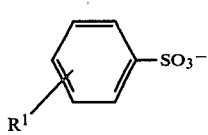

wherein R¹ is hydrogen, alkyl of from 1 to 6 carbon atoms, methoxy, chlorine, or bromine; R²SO⁻₄ wherein R² is alkyl of from 1 to 3 carbon atoms; and (b) a pharmacologically acceptable carrier.

The invention sought to be patented in its second subgeneric process aspect resides in the concept of a method of relieving bronchial spasm and facilitating breathing in warm-blooded animals which comprises administering to a warm-blooded animal in need thereof, by aerosol route, an amount sufficient to relieve bronchial spasm and facilitate breathing in said warm-blooded animal of a composition comprising:

(a) dl(2-hydroxyethyl)dimethyl[1-methyl-2-(phenothiazin-10-yl)ethyl]ammonium chloride; and (b) a pharmacologically acceptable carrier.

The invention sought to be patented in its principal composition aspect resides in the concept of a bronchodilating and spasm reducing composition formulated for inhalation therapy from a nebulizer such that each dose comprises:

(a) a bronchodilating and bronchial spasm reducing amount of a compound of the formula:

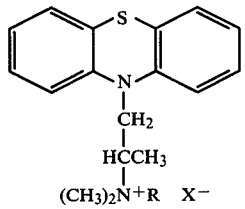

wherein R is hydroxyalkyl of from 2 to 4 carbon atoms with the proviso that the hydroxyl group is not borne on the same carbon atom which is bonded to nitrogen; X is a pharmacologically acceptable anion; and (b) a pharmacologically acceptable inhalation carrier, in an amount sufficient to provide a composition administerable by the oral inhalation route.

The invention sought to be patented in its first subgeneric composition aspect resides in the concept of a bronchodilating and bronchial spasm reducing composition formulated for inhalation therapy from a nebulizer such that each dose comprises:

(a) a bronchodilating and bronchial spasm reducing amount of a compound of the formula:

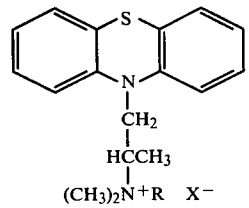

wherein R is hydroxyalkyl of from 2 to 4 carbon atoms with the proviso that the hydroxyl group is not borne on the same carbon atom which is bonded to nitrogen; X is OH⁻, Cl⁻, Br⁻, I⁻, NO⁻₃,

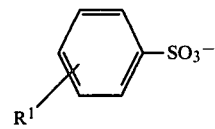

wherein R¹ is hydrogen alkyl of from 1 to 6 carbon atoms, methoxy, chlorine, or bromine; R²SO⁻₄, wherein R² is alkyl of from 1 to 3 carbon atoms; and (b) a pharmacologically acceptable inhalation carrier, in an amount sufficient to provide a composition administerable by the oral inhalation route.

The invention sought to be patented in its second subgeneric composition aspect resides in the concept of a bronchodilating and bronchial spasm reducing composition formulated for inhalation therapy from a nebulizer such that each dose comprises:

(a) a bronchodilating and bronchial spasm reducing amount of dl-(2-hydroxyethyl)dimethyl[1-methyl-2-(phenothiazin-10-yl)ethyl]ammonium chloride; and (b) a pharmacologically acceptable inhalation carrier, in an amount sufficient to provide a composition administerable by the oral inhalation route.

DESCRIPTION OF THE INVENTION

The quaternary salts of promethazine utilized in the processes and compositions of the instant invention may be conveniently prepared, for example, from promethazine itself or from 10-(2-aminopropyl)phenothiazine (U.K. Pat. No. 731,016) by methods familiar to those skilled in the art (see for example, U.K. Pat. No. 881,379). Many of the salts contemplated by the instant invention be prepared, conveniently, by mixing a solution of promethazine and the salt forming reagent in a solvent in which both materials will be soluble and in which the product quaternary salt will be insoluble. The product salt is then easily collected by filtration. Examples of such solvents are acetone, benzene, ether and the like. The salt, in some cases, will form spontaneously at room temperature but in certain instances heating for several hours (e.g. about 48 hours) may be required. Those skilled in the art will readily be able to ascertain those instances when heating is required. The use of methods other than that described above for preparing and isolating quaternary salts is also contemplated. Thus a solvent may be employed in which promethazine, the salt forming reagent, and the quaternary salt may all be substantially soluble (e.g. ethanol). In this instance, after reaction, the salt may be collected by, for example, concentration or evaporation of the solvent, and it may be purified by, for example, recrystallization. Other methods will suggest themselves to those skilled in the art.

The salt forming reagents contemplated by the invention are those of the general formula R-Y wherein R is hydroxyalkyl of from 2 to 4 carbon atoms with the proviso that the hydroxyl group is not borne on the same carbon atom which is bonded to Y, and Y is a substituent commonly referred to in the art as a "leaving group" (see for example, J. D. Roberts and M. C. Caserio, Basic Principles of Organic Chemistry, W. A. Benjamin Inc., New York, 301 [1965]). The hydroxyalkyl radicals contemplated by the instant invention are for example, $CH_2CH_2OH$, $CH_2CH_2CH_2OH$, $CH_2CH_2CH_2CH_2OH$, $CH_2CH(OH)CH_3$, $CH_3CHCH_2OH$, $CH_3CHCH_2CH_2OH$, $CH_3CH_2CHCH_2OH$, $(CH_3)_2CCH_2OH$, and the like. The preferred Y substituents contemplated by the instant invention are Cl, Br, I, $CH_3SO_3$, $C_6H_5SO_3$ and the like; other suitable Y substituents will suggest themselves to those skilled in the art.

It will be obvious to those skilled in the art that the substituent Y becomes an anion subsequent to the quaternizing reaction and that it may or may not be identical to the desired anion X. It will also be obvious that certain anions may be introduced into the quaternary salt by, for example, an exchange process, thus making possible, if desired, exchange of the produced anion Y, by a desired anion X. Anion exchange methods will be familiar to those skilled in the art; for example, chromatographic means may be employed.

Examples of salt forming reagents contemplated by the instant invention are 2-chloroethanol, 2-bromoethanol, 3-chloropropanol, 2-bromopropanol, 3-chlorobutanol, 4-bromobutanol, 3-bromo-2-butanol, and the like.

Promethazine itself, is a well-known medicament and its synthesis by several different methods has been described (see for example, U.S. Pat. Nos. 2,530,451; 2,607,773).

Because the promethazine molecule contains in its structure an assymetric carbon atom, the molecule is capable of existing as the d,l racemic mixture as well as in its pure d and pure l forms. Thus, the instant invention contemplates the quaternary salts of dl-promethazine as well as the quaternary salts of d-promethazine and the quaternary salts of l-promethazine. Methods for separating dl-promethazine into its enantiomeric constituents, substantially free from each other, will be familiar to those skilled in the art [see for example Toldy, L., et al., Acta. Chim. Acad. Sci. Hung., 19, 273 (1959); C. A. $3425^h$(1960)]. Methods for producing quaternary salts from either the d or l isomer are substantially identical to those methods useful for the d,l racemic mixture. In addition, an aassymetric center may be introduced into the molecule because of the particular hydroxyalkyl group utilized. Thus, for example, the hydroxyalkyl group $CH_3CHCH_2CH_2OH$ will add a center of assymetry to the molecule and an isomeric mixture will result. Methods for separating such isomeric mixtures will be familiar to those skilled in the art. The instant invention also contemplates these pure isomers as well as their isomeric mixtures.

For purposes of this invention, a preferred quaternary salt of promethazine is N-hydroxyethyl promethazine chloride dl-(2-hydroxyethyl)dimethyl-[1-methyl-2-(phenothiazin-10-yl)-ethyl]ammonium chloride. This salt is readily prepared by methods known to those skilled in the art. Thus, for example, on mixing a solution of dl-promethazine and 2-chloroethanol in a suitable solvent such as methyl ethyl ketone at, for example, reflux temperature for 48 hours, the quaternary salt N-hydroxyethylpromethazine chloride is obtained. The salt obtained in this manner may be purified by, for example, recrystallization from 2-propanol, and is suitable for use in the method and compositions of the invention. Other quaternary salts such as N-hydroxyethylpromethazine iodide may be prepared by similar methods which will be familiar to those skilled in the art.

In practicing the method of the invention, the instant compositions are administered by oral or nasal inhalation, oral inhalation being the preferred route. Inhalation therapy (aerosols and solution for nebulizers) combines the advantages of maintenance and moderately-acute stage therapy in one convenient dosage unit.

The daily dose requirements vary with the particular compositions being employed, the severity of the symptoms being presented, and the animal being treated. The dosage varies with the size of the animal. With large animals (about 70 kg. body weight), by the oral inhalation route, with for example, a hand nebulizer or a pressurized aerosol dispenser, the dose is from about 50 micrograms to about 5 milligrams, and preferably from about 100 micrograms to about 2 milligrams, approximately every 4 hours, or as needed.

For administration by the oral or nasal inhalation route with conventional nebulizers or by oxygen aerosolization it is convenient to provide the instant active ingredients suspended or dissolved in a pharmacologically acceptable inhalation carrier. Examples of such carriers are distilled water, water/ethanol mixtures, and physiological saline solution; other such carriers will suggest themselves to those skilled in the art. Entirely conventional additives may be employed in these dosage forms to stabilize or to provide isotonic media; for example, sodium chloride, sodium citrate, glucose, citric acid, sodium bisulfite, and the like can be employed. For convenience, the instant active ingredients are provided, preferably at concentrations of about 1 part medicament to form about 20 to about 100 parts by weight of total mixture.

For administration as a self-propelled dosage unit for administering the active ingredient in aerosol form suitable for inhalation therapy, the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispersing agent such as oleyl alcohol. Suitable means to employ the aerosol inhalation therapy technique are described, for example, in U.S. Pat. Nos. 2,868,691 and 3,095,355.

The following examples further illustrate the best mode contemplated by the inventor for the practice of the invention.

EXAMPLE 1

Anesthetized (Pentobarbitol-urethane) guinea pigs were artificially respired at a constant positive air pressure (Starling miniature pump) and changes in tidal air during inspiration were recorded, according to the method of Rosenthale et al., Int. Arch. Pharmacol., 172, 91 (1968). The bronchoconstrictor agent acetylcholine was administered intravenously at doses of 1 to 30 µg/kg. depending on each animal's sensitivity to this compound, and control responses to acetylcholine were thus established. Bronchoconstrictor agents raise the resistance of the lungs to inflation thereby decreasing the tidal air flow. A solution of the test compound was then administered by aerosol, in physiological saline, and the animals were then challenged again with acetylcholine and the degree of inhibition of bronchoconstriction by the test compound was thus determined.

| Compound | Dose (µg as cation) in saline | No. Pigs | Mean % Inhibition vs. Acetylcholine |
|---|---|---|---|
| N-Hydroxyethyl-pro- | 0.15 | 1 | 0 |

-continued

| Compound | Dose (μg as cation) in saline | No. Pigs | Mean % Inhibition vs. Acetylcholine |
|---|---|---|---|
| methazine chloride | 1.5 | 3 | 54.7 |
|  | 15 | 2 | 78.5 |

EXAMPLE 2 dl-(2-Hydroxyethyl)Dimethyl-[1-Methyl-2-(Phenothiazin-10-yl)-Ethyl]Ammonium Chloride dl-Promethazine free base (10 g.) and 2-chloroethanol (50 cc.) were heated on a steam bath for 5 hours and allowed to stand at room temperature for 48 hours. The reaction solution was added dropwise into anhydrous ether (300 cc.), and the white precipitate which formed was collected by vacuum filtration, 11.0 g., m.p. 218°–220° C. d. This solid, dl-(2-hydroxyethyl)dimethyl-[1-methyl-2-(phenothiazin-10-yl)-ethyl]ammonium chloride, was recrystallized from i-propanol yielding 8.1 g. of white solid, m.p. 228°–229° C.

Analysis for: $C_{19}H_{25}ClN_2OS$: Calculated: C, 62.53; H, 6.90; N, 7.68; Cl, 9.72. Found: C, 62.81; H, 7.04; N, 7.69; Cl, 9.71.

The subject matter which the Applicant regards as his invention is particularly pointed out and distinctly claimed as follows:

1. A method of relieving bronchial spasm and facilitating breathing in warm-blooded animals which comprises administering to a warm-blooded animal in need thereof, by aerosol route, an amount sufficient to relieve bronchial spasm and facilitate breathing in said warm-blooded animal of a composition comprising:

(a) a compound of the formula:

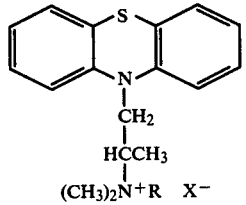

wherein R is hydroxyalkyl of from 1 to 4 carbon atoms with the proviso that the hydroxyl group is not borne on the same carbon atom which is bonded to nitrogen; X is a pharmacologically acceptable anion; and (b) a pharmacologically acceptable carrier.

2. The method of claim 1 which comprises administering to a warm-blooded animal in need thereof, by aerosol route, an amount sufficient to relieve bronchial spasm and facilitate breathing in said warm-blooded animal of a composition comprising:

(a) a compound of the formula:

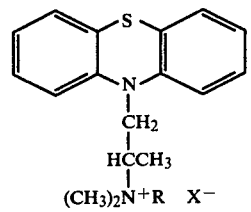

wherein R is hydroxyalkyl of from 2 to 4 carbon atoms with the proviso that the hydroxyl group is not borne on the same carbon atom which is bonded to nitrogen; X is $Oh^-$, $Cl^-$, $Br^-$, $I^-$, $NO^-_3$,

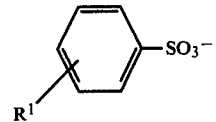

wherein $R^1$ is hydrogen, alkyl of from 1 to 6 carbon atoms, methoxy, chlorine, or brine; $R^2SO^-_4$ wherein $R^2$ is alkyl of from 1 to 3 carbon atoms; and (b) a pharmacologically acceptable carrier.

3. The method of claim 1 wherein R is $CH_2CH_2OH$.

4. The method of claim 1 wherein X is $Cl^-$.

5. The method of claim 1 wherein the compound in (a) is dl-(2-hydroxyethyl)dimethyl[1-methyl-2-(phenothiazin-10-yl)ethyl]ammonium chloride.

* * * * *